United States Patent [19]

Tessier et al.

[11] Patent Number: 4,808,210
[45] Date of Patent: Feb. 28, 1989

[54] HERBICIDAL METHOD OF USING 5-PYRAZOLONES

[75] Inventors: Jean Tessier, Vincennes; Pierre Girault, Paris, both of France

[73] Assignee: Roussel Uclaf, Paris, France

[21] Appl. No.: 96,364

[22] Filed: Sep. 11, 1987

[30] Foreign Application Priority Data

Sep. 18, 1986 [FR] France ................................ 86 13050

[51] Int. Cl.$^4$ ............................................ A01N 43/56
[52] U.S. Cl. ............................................ 71/92; 71/90;
544/298; 544/300; 544/310; 544/316; 544/317;
544/322; 544/324; 544/327; 544/328; 544/331;
546/279; 548/182; 548/183; 548/184; 548/195;
548/365; 548/367
[58] Field of Search .............. 548/365, 367, 182, 183,
548/184, 195; 71/92, 90; 544/298, 300, 310,
316, 317, 322, 324, 327, 328, 331; 546/279

[56] References Cited

U.S. PATENT DOCUMENTS 4,081,596   3/1978   Moller et al. ....................... 548/367
4,256,902   3/1981   Boschi et al. ....................... 548/365

FOREIGN PATENT DOCUMENTS 2029889  10/1970  France ................................ 548/365

Primary Examiner—Mary C. Lee
Assistant Examiner—Kurt G. Briscoe
Attorney, Agent, or Firm—Bierman and Muserlian

[57] ABSTRACT

A 5-pyrazolone of the formula

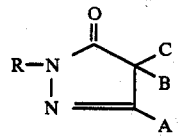

wherein R is selected from the group consisting of mono- and polycyclic aromatic of 6 to 14 carbon atoms, heterocyclic optionally substituted with phenyl,

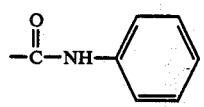

and benzyl, all optionally substituted with at least one member of the group consisting of fluorine, chlorine, bromine, —CF$_3$, optionally unsaturated alkyl of 1 to 8 carbon atoms and the radical OZ in which Z is an optionally unsaturated alkyl of 1 to 8 carbon atoms or an acyl of a carboxylic acid of 1 to 6 carbon atoms, A is selected from the group consisting of halogen, —CF$_3$ and —CN, B and C are individually selected from the group consisting of hydrogen, halogen, —OH, —OR' and R' is optionally unsaturated alkyl of 1 to 8 carbon atoms, acyl of 1 to 6 carbon atoms, alkyl sulfonyl of 1 to 8 carbon atoms, aryl sulfonyl of 6 to 18 carbon atoms and benzyl optionally substituted with a member of the group consisting of fluorine, chlorine, bromine, —CF$_3$, optionally unsaturated alkyl of 1 to 8 carbon atoms, optionally unsaturated alkyl and haloalkyl of 1 to 8 carbon atoms interrupted with at least one heteroatom, with the proviso that B and C can not both be fluorine or —OH having herbicidial activity.

2 Claims, No Drawings

HERBICIDAL METHOD OF USING 5-PYRAZOLONES

STATE OF THE ART

European patent application Ser. No. 165,448 and Chem. Abst. Vol. 85, No. 1-05-07 (1976) and Chem. Abst. Vol. 85, No. 21-22-11 (1976) describe certain pyrazolones.

OBJECTS OF THE INVENTION

It is an object of the invention to provide the novel 5-pyrazolones of formula I and a process for their preparation.

It is another object of the invention to provide novel herbicidal compositions and a novel method of combatting weeds.

These and other objects and advantages of the invention will become obvious from the following detailed description.

THE INVENTION

The novel compounds of the invention are 5-pyrazolones of the formula

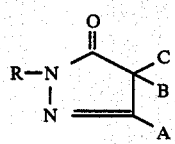

wherein R is selected from the group consisting of mono- and polycyclic aromatic of 6 to 14 carbon atoms, heterocyclic optionally substituted with phenyl,

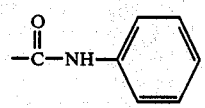

and benzyl, all optionally substituted with at least one member of the group consisting of fluorine, chlorine, bromine, —$CF_3$, optionally unsaturated alkyl of 1 to 8 carbon atoms and the radical OZ in which Z is an optionally unsaturated alkyl of 1 to 8 carbon atoms or an acyl of a carboxylic acid of 1 to 6 carbon atoms, A is selected from the group consisting of halogen, —$CF_3$ and —CN, B and C are individually selected from the group consisting of hydrogen, halogen, —OH, —OR' and R' is optionally unsaturated alkyl of 1 to 8 carbon atoms, acyl of 1 to 6 carbon atoms, alkyl sulfonyl of 1 to 8 carbon atoms, aryl sulfonyl of 6 to 18 carbon atoms and benzyl optionally substituted with a member of the group consisting of fluorine, chlorine, bromine, —$CF_3$, optionally unsaturated alkyl of 1 to 8 carbon atoms, optionally unsaturated alkyl and haloalkyl of 1 to 8 carbon atoms interrupted with at least one heteroatom, with the proviso that B and C can not both be fluorine or —OH.

Examples of R are monocyclic aryl such as phenyl, polycyclic aryl such as naphthyl, heterocycle connected through a carbon atom such as thiazolyl, pyridinyl and pyrimidyl; when R is substituted by optionally substituted alkyl, examples of alkyl are methyl, ethyl, n-propyl, isopropyl, n-butyl, isobutyl, tert.-butyl, n-pentyl and hexyl and examples of alkenyl are allyl or 2-methyl-allyl.

When A, B or C are halogen, it is preferably chlorine, bromine or iodine and when B,C, Z or R' are alkyl, it is preferably methyl, ethyl, n-propyl, isopropyl, n-butyl, tert.-butyl, n-pentyl or n-hexyl. When B or C are alkyl or haloalkyl interrupted by a heteroatom, the heteroatom is preferably oxygen and the halogens are preferably bromine or chlorine.

When Z or R' are acyl, they are preferably acetyl or propionyl. When R' is alkylsulfonyl or arylsulfonyl, it is perferably methylsulfonyl, ethylsulfonyl or benzylsulfonyl.

Among the preferred compounds of formula I are those wherein R is phenyl optionally substituted with at least one bromine or chlorine, those wherein A is chlorine, —$CF_3$ or —CN and those wherein B and C are individually hydrogen, chlorine, bromine, alkyl of 1 to 6 carbon atoms or allyl.

Specific preferred compounds of formula I are 1-(3,4-dichlorophenyl)-3,4-dichloro-4-(2-methylpropyl)-5-pyrazolone, 1-(3-chloro-4-bromophenyl)-3-trifluoromethyl-4-chloro-4-methyl-5-pyrazolone, 1-(3,5-dichlorophenyl)-3,4-dichloro-4-methyl-5-pyrazolone and 1-(3,4-dichlorophenyl)-3,4-dichloro-4-n-propyl-5-pyrazolone.

The novel process of the invention for the preparation of the compounds of formula I comprises reacting a compound of the formula $$H_2N—NH—R \qquad II$$

wherein R has the above definition with a compound of the formula

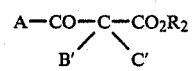

wherein A has the above definition and B' and C' have the same definition of B and C except for —OH and —OR' and $R_2$ is alkyl of 1 to 8 carbon atoms to obtain a compound of the formula

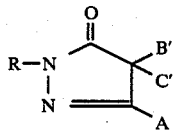

wherein A, R, B' and C' have the above definitions and when B' or C' are hydrogen, optionally reacting the latter with a halogenating agent to obtain a compound of formula I where B' or C' or B' and C' are halogen or reacting the compound of formula $I_4$ with an oxidation agent to obtain a compound of formula I wherein B' or C' is hydroxy and optionally reacting the latter with a halogenating agent or an agent capable of introducing an alkyl, acyl, arylsulfonyl or alkylsulfonyl to obtain the corresponding compound of formula I.

In a preferred mode of the process of the invention, the reaction between the compounds of formulae II and III is effected in an alcohol and when R is

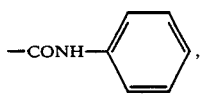

the resulting product is treated with a base such as ammonia to obtain the cyclized product of formula I. The halogenating agent is preferably the molecular halogen.

In a variation of the process of the invention, the compound of formula II is reacted with a compound of the formula

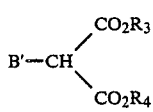
IV wherein B' has the above definition and $R_3$ and $R_4$ are individually alkyl of 1 to 6 carbon atoms to obtain a compound of the formula

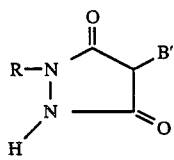
V and reacting the latter with a chlorinating agent to obtain if B' is other than hydrogen a compound of the formulae

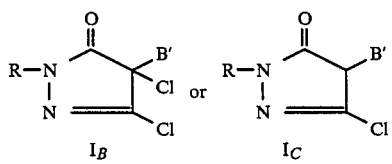

and if B' is hydrogen a compound of the formula

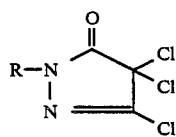
$I_D$

Optionally, the compound of formula $I_C$ may be reacted with chlorine to obtain the compound of formula $I_D$ or with an oxidation agent to obtain a compound of the formula

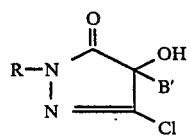
$I_E$ which may be reacted with a halogenation agent or an agent capable of introducing alkyl, acyl, alkylsulfonyl or arylsulfonyl to obtain the corresponding compound of formula I.

Preferably, the reaction between the compounds of formulae II and IV is effected at 100° to 200° C. and the chlorinating agent is a mixture of phosphorus pentachloride and phosphorus oxychloride.

In another variation of the process of the invention, a compound of the formula

R—NH$_2$    VI is reacted with a diazotization agent to obtain the corresponding diazonium salt which is reacted with a compound of the formula

VII wherein B' has the above definition and alk$_1$ and alk$_2$ are individually alkyl of 1 to 8 carbon atoms to obtain a compound of the formula

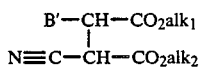
$I_F$ and optionally reacting the latter with a halogenating agent to obtain when B' is hydrogen a compound of the formula

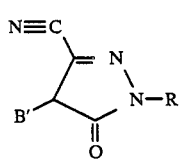
$I_G$ or when B' is other than hydrogen a compound of the formula

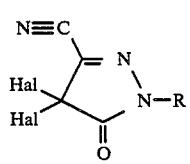
$I_H$ or reacting the compound of formula $I_F$ with an oxidation agent to obtain a compound of the formula

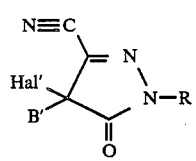
($I_I$)

which may be reacted with a halogenation agent or an agent capable of introducing alkyl, acyl, alkylsulfonyl or arylsulfonyl to obtain the corresponding compound of formula I. Preferably, the diazotization agent is an alkyl nitrite or an alkali metal nitrite such as sodium nitrite or potassium nitrite.

The novel herbicidal compositions of the invention are comprised of an herbicidally effective amount of at least one compound of formula I and a carrier. The compositions are useful for selectively killing weeds in cereal crops such as wheat, barley, oats, and corn or rice, cotton and soy beans.

The compositions of the invention may be in the form of powders, granules, suspensions, emulsions, or solutions containing the active principle, for example, mixed with a vehicle and/or an anionic, cationic or non-ionic tensio-active agent, ensuring amongst other things, a uniform dispersion of the substances of the composition. The vehicle used maybe a liquid such as water, alcohol, hydrocarbons or other organic solvents, a mineral, animal or vegetable oil, or a powder such as talc, clays, silicates or kieselguhr.

The solid compositions in the form of a powder for dusting, wettable powders or granules may be prepared by grinding the active compound with an inert solid or by impregnation of a solid support with a solution of the active principle in a solvent which is then evaporated.

In addition to a vehicle and/or a tensio-active agent, the compositions contain as well other pesticides and substances having properties which have an influence on the growth of plants.

The compositions of the invention are, of course, applied in doses which are sufficient to exert their herbicide activities. The quantities of active material in the compositions vary as a function of the vegetation to be destroyed, the nature of the terrain, the atmospheric conditions and the state of advancement of the vegetation to be destroyed.

The herbicide compositions according to the invention contain in general from 10 to 80% by weight and, preferably from 10 to 50% by weight of active material. When the compounds of formula I are used as herbicides, the quantities of active substance used vary before sprouting preferably between 0.1 and 5 kg/ha and after sprouting, preferably between 0.5 and 2 kg/ha.

The novel method of the invention for selectively killing weeds in a useful crop comprises applying to the useful crop an herbicidally effective amount of at least one compound of formula I. The compounds may be applied peremergence or post-emergence.

In the following examples there are described several preferred embodiments to illustrate the invention. However it is to be understood that the invention is not intended to be limited to the specific embodiments.

EXAMPLE 1

1-(4-bromo-3-chlorophenyl)-3-trifluoromethyl-4-allyl-4-chloro-5-pyrazolone (method I)

STEP A:
1-(4-bromo-3-chlorophenyl)-3-trifluoromethyl-4-allyl-5-pyrazolone

A mixture of 12.1 g of ethyl 2-allyl-4,4,4-trifluoroacetoacetate, 10 g of 4-bromo-3-chlorophenylhydrazine and 40 ml of ethanol was refluxed for 19 hours and 20 ml of water and 20 ml of acetic acid were then added. The mixture was refluxed for 22 hours and then allowed to cool. After extraction with ether, the extracts were washed with a saturated aqueous solution of sodium bicarbonate, then with water, dried over anhydrous sodium sulfate and concentrated under vacuum to obtain 18.7 g of product which was chromatographed over silica and eluted with a hexane-ethyl ether (1-1) mixture to obtain 5.30 g of 1-(4-bromo-3-chlorophenyl)-3-trifluoromethyl-4-allyl-5-pyrazolone melting at 117° C. after taking up in pentane.

STEP B:
1-(4-bromo-3-chlorophenyl)-3-trifluoromethyl-4-allyl-4-chloro-5-pyrazolone A mixture of 4.06 g of the product of Step A and 150 ml of carbon tetrachloride was cooled to 0° C. and 17.2 ml of chlorine in solution in carbon tetrachloride (1.55 mole per liter) were added. When the reaction was complete, the product was washed with a saturated solution of sodium bicarbonate, with water, dried, treated with active charcoal and stirred for 15 hours, filtered and concentrated to obtain 51 g of 1-(4-bromo-3-chlorophenyl)-3-trifluoromethyl-4-allyl-4-chloro-5-pyrazolone.

EXAMPLE 2

1-(phenylcarbamoyl)-3-trifluoromethyl-5-pyrazolone (method 2)

STEP A: Ethyl 4,4,4-trifluoro-3-(phenyl semi-carbazone)-butyrate 15.1 g of 4-phenyl semi-carbazide, 18.4 g of ethyl trifluoroacetylacetate, 80 ml of ethanol and 10 ml of acetic acid were refluxed with stirring for 5 hours and the mixture was cooled and ice was added. The crystals were separated, washed and dried to obtain 14 g of crude product which was purified by solution in methylene chloride, filtration of the isoluble part and distillation to dryness under reduced pressure. After drying, 11.2 g of ethyl 4,4,4-trifluoro-3-(phenyl semicarbazone)-butyrate melting at 162°-163° C. were obtained.

STEP B:
1-(phenylcarbamoyl)-3-trifluoromethyl-5-pyrazolone 10 g of ethyl 4,4,4,-trifluoro-3-(phenyl semi-carbazone)-butyrate and 200 ml of ammonia water were stirred for 3 hours and 200 ml of water were added. The insoluble part was filtered off and washed with water. The combined filtrates were acidified with dilute hydrochloric acid and the precipitate formed was separated, washed and dried to obtain 7.20 g of 1-(phenyl-carbamoyl)-3-trifluoromethyl-5-pyrazolone melting at 109°-110° C.

EXAMPLE 3

1-(3,5-dichlorophenyl)-3,4-dichloro-4-methyl-5-pyrazolone (method 3)

STEP A:
1-(3,5-dichlorophenyl)-4-methylpyrazolidine-3,5-dione

A solution of 17.55 g of 3,4-dichlorophenyl-hydrazine and 35 g of diethyl methylmalonate was heated at 180° C. for 5 hours and distilled with the distilled products being eliminated. The remainder was cooled and taken up in methylene chloride. The organic phase was extracted with 2N dilute sodium hydroxide, washed with methylene chloride, treated with active charcoal, and acidified to pH 1 with hydrochloric acid. The precipitate was separated, washed with water and dried under reduced pressure to obtain 16.9 g of 1-(3,5-dichlorophenyl)-4-methylpyrazolidine-3,5-dione melting at 95°-100° C.

STEP B:
1-(3,5-dichlorophenyl)-3,4-dichloro-4-methyl-5-pyrazolone 21.6 g of the product of Step A, 90 ml of phosphorus oxychloride and 56 g of phosphorus pentachloride were refluxed for 16 hours and the mixture was cooled and poured on to ice. The precipitate was separated, washed with water and dried to obtain 19.3 g of crude product which was chromatographed over silica by eluting with a methylene chloride-hexane (3-7) mixture to obtain 4.35 g of 1-(3,5-dichlorophenyl)-3,4-dichloro-4-methyl-5-pyrazolone melting at 77° C.

EXAMPLE 4

1-(3,4-dichlorophenyl)-3-cyano-4-chloro-4-methyl-5-pyrazolone (method 4)

STEP A:

1-(3,4-dichlorophenyl)-3-cyano-4-methyl-5-pyrazolone 10 g of sodium nitrite and 30 ml of water were added with stirring into a mixture of 22.7 g of 3,4-dichloroaniline, 100 ml of water and 30 ml of concentrated hydrochloric acid. The resulting mixture was stirred for 15 minutes at 0° C. and the reacting solution was poured at 15°-20° C. into a solution of 33 g of ethyl 3-cyano-3-methyl succinate and 600 ml of pyridine. The mixture was stirred for 2 hours at 20° C. and 186 ml of triethylamine and 310 ml of a 2% aqueous solution of sodium hydroxide were introduced simultaneously. The mixture was stirred for 3 hours at 20° C. and was then poured into 1,500 ml of iced water with stirring. The pH was adjusted to by concentrated hydrochloric acid. After separating, washing with water and drying under reduced pressure, 38 g of the crude product were obtained which was crystallized from acetonitrile and dried to obtain 27 g of 1-(3,4-dichlorophenyl))-3-cyano-4-methyl-5-pyrazolone melting at 210° C.

STEP B:

1-(3,4-dichlorophenyl)-3-cyano-4-chloro-4-methyl-5-pyrazolone 41.5 ml of an 8.1% solution of chlorine in carbon tetrachloride were introduced at about 20° C. into a solution of 12.7 g of 1-(3,4-dichlorophenyl)-3-cyano-4-methyl-5-pyrazolone in 100 ml of chloroform and the mixture was stirred for 1 hour at 20° C. After distillation of the solvents under reduced pressure, 17 g of a yellow oil were obtained which was purified by chromatography over silica. Elution with a methylene chloride-hexane mixture (8-2) to yielded 12.2 g of 1-(3,4-dichlorophenyl)-3-cyano-4-chloro-4-methyl-5-pyrazolone melting at 68°-69° C.

The following compounds were prepared by the method indicated in the Examples.

EXAMPLE 5

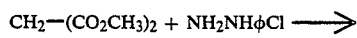

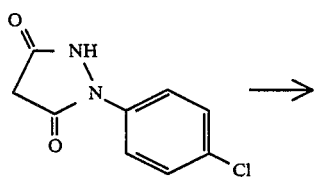

MP = 203° C.

-continued

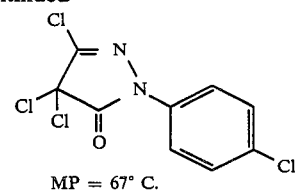

MP = 67° C.
Operating Method 3

EXAMPLE 6

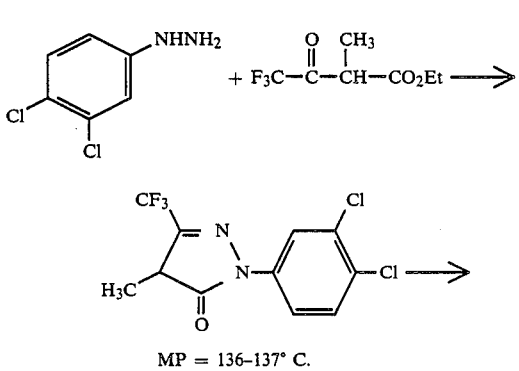

MP = 136-137° C.

MP = 62-63° C.
Operating Method 1

EXAMPLE 7

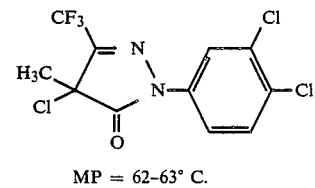

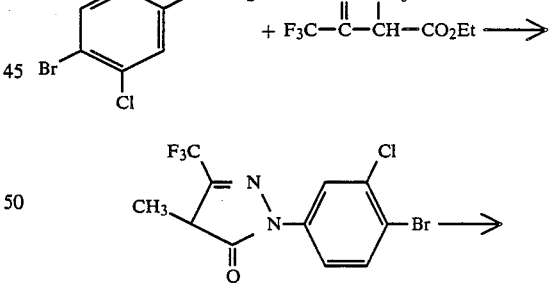

MP = 66-67° C.
Operating Method 1

EXAMPLE 8

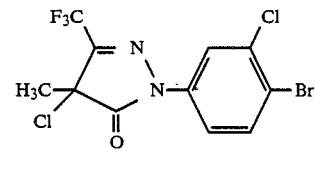

Operating Method 1

-continued
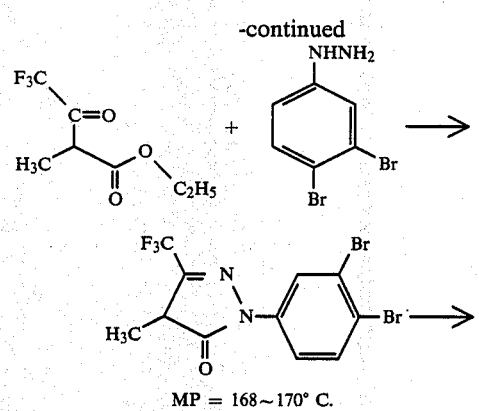
MP = 168~170° C.
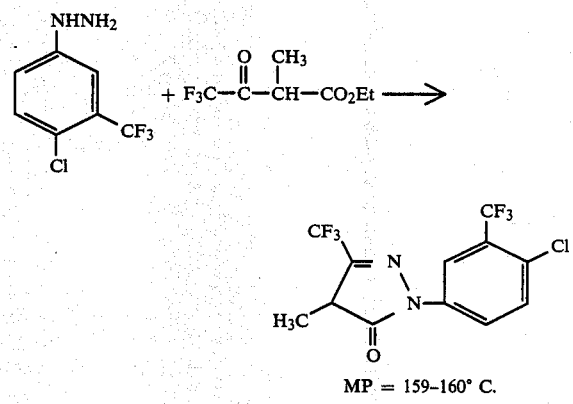
MP = 62-64° C.
EXAMPLE 9
Operating Method 1
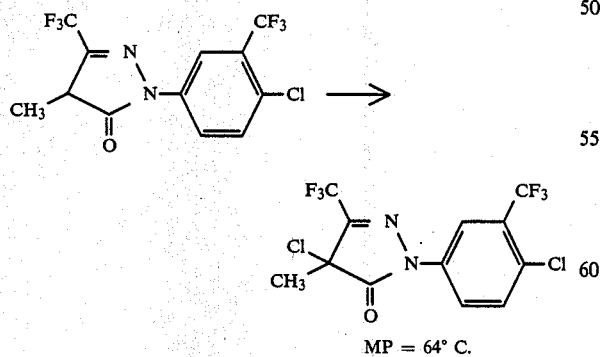
MP = 159-160° C.
EXAMPLE 10
Operating Method 1
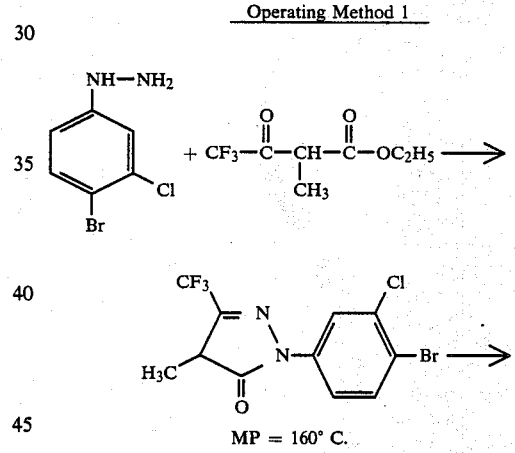
MP = 64° C.
EXAMPLE 11
Operating Method 3
-continued
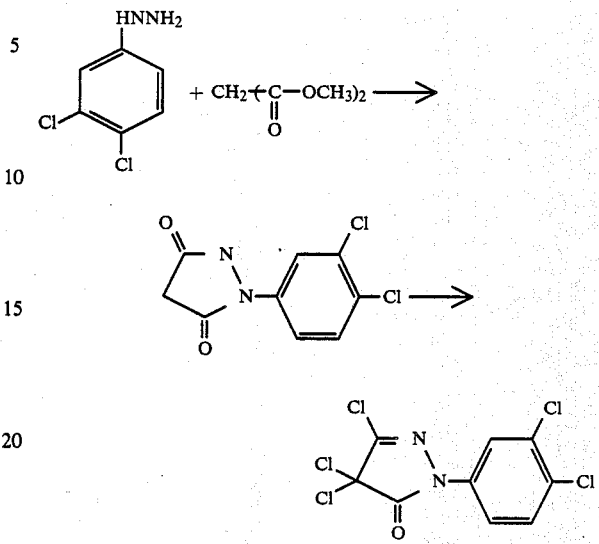
EXAMPLE 12
Operating Method 1
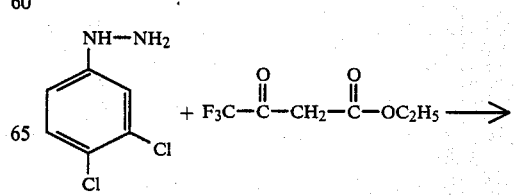
MP = 160° C.
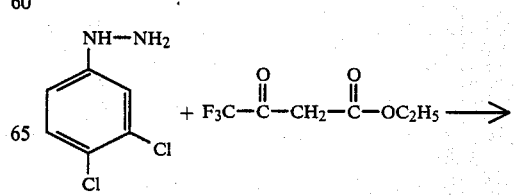
MP = 93~94° C.
EXAMPLE 13
Operating Method 1

-continued
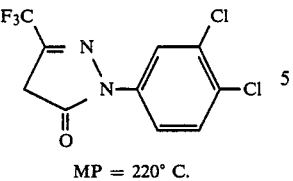
MP = 220° C.
EXAMPLE 14
Operating Method 1
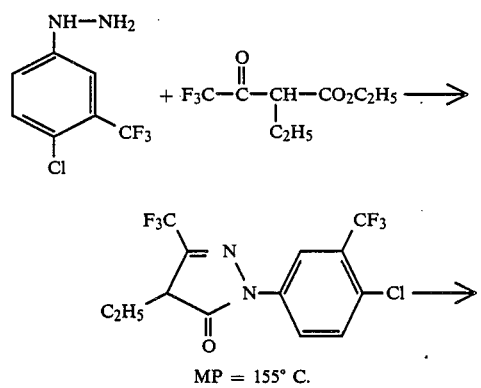
MP = 155° C.
MP = 38–39° C.
EXAMPLE 15
Operating Method 1
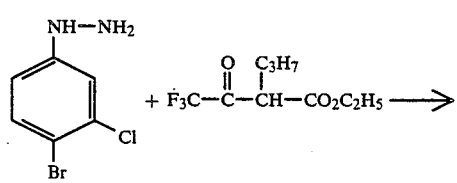
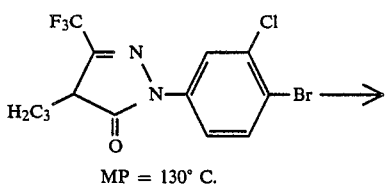
MP = 130° C.
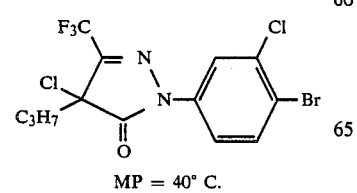
MP = 40° C.
EXAMPLE 16
Operating Method 1
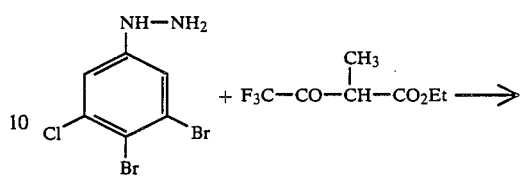
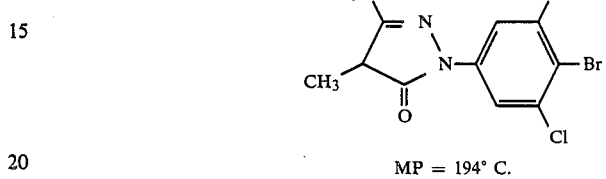
MP = 194° C.
EXAMPLE 17
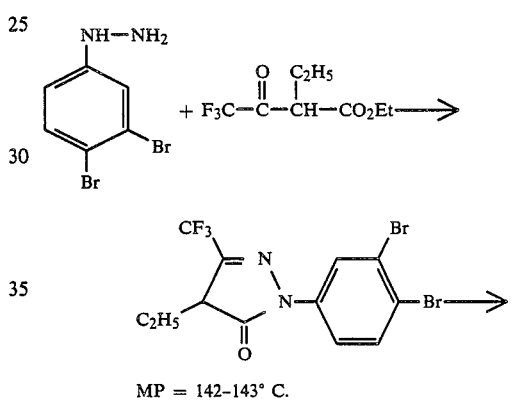
MP = 142–143° C.
MP = 90~91° C.
Operating Method 1
EXAMPLE 18
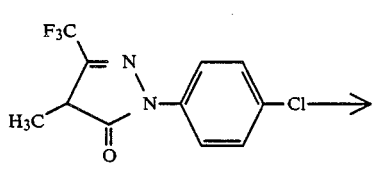
MP = 175–176° C.

-continued
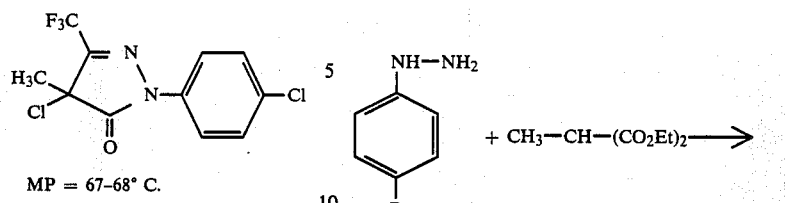
MP = 67–68° C.
Operating Method 1
EXAMPLE 19
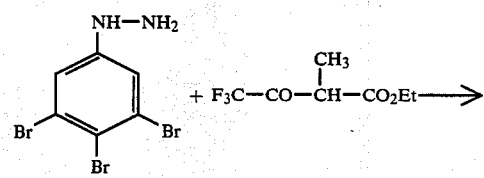
MP = 202° C.
Operating Method 1
EXAMPLE 20
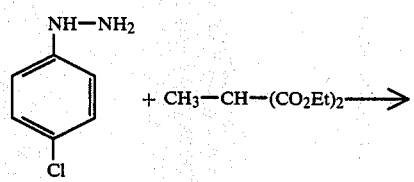
MP = 157° C.
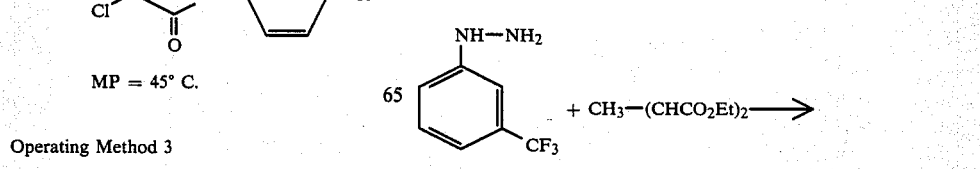
MP = 45° C.
Operating Method 3
EXAMPLE 21
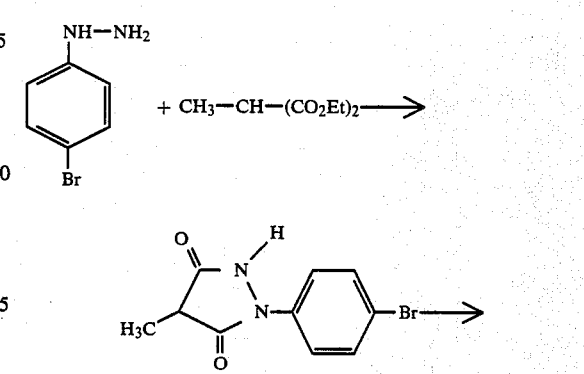
MP = 40° C.
Operating Method 3
EXAMPLE 22
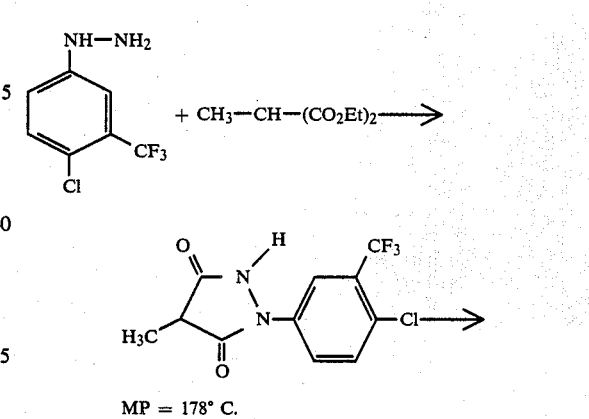
MP = 178° C.
MP = 57° C.
Operating Method 3
EXAMPLE 23

-continued
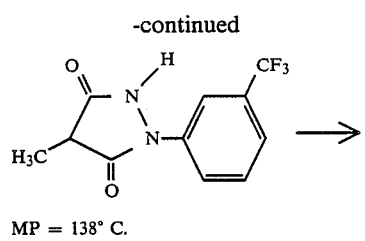
MP = 138° C.
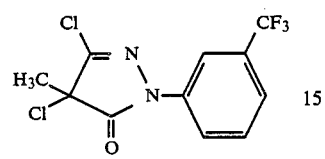
Operating Method 3
EXAMPLE 24
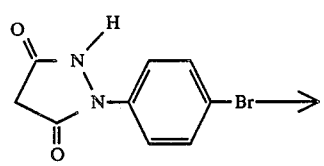
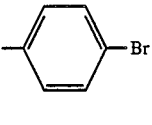
Operating Method 3
EXAMPLE 25
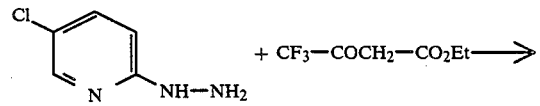
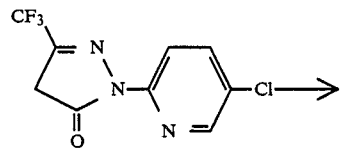
MP = 108° C.
Operating Method 1
EXAMPLE 26
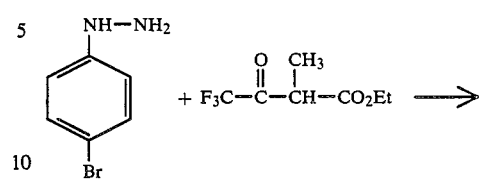
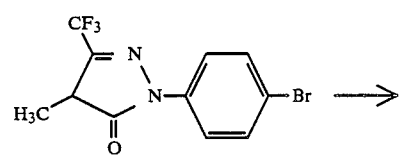
MP = 160~161° C.
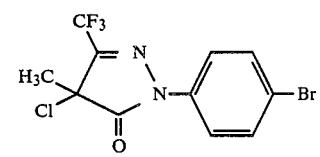
MP = 75~76° C.
Operating Method 1
EXAMPLE 27
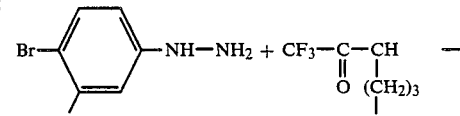
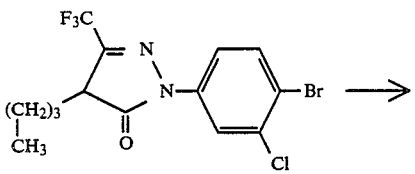
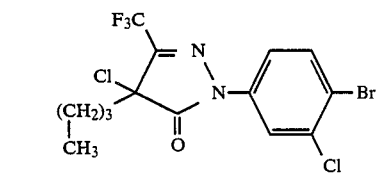
Operating Method 1
EXAMPLE 28
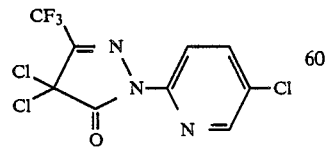
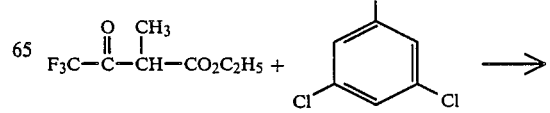

MP = 173-174° C.

MP = 90-91° C.

Operating Method 1

EXAMPLE 29

MP = 80° C.

Operating Method 1

EXAMPLE 30

MP = 142~143° C.

-continued
Operating Method 2

EXAMPLE 31

MP = 150~151° C.

MP = 114~115° C.

Operating Method 2

EXAMPLE 32

Operating Method 3

EXAMPLE 33

$+ CH_3-CH-(CO_2Et)_2 \longrightarrow$

MP = 100° C.

-continued
Operating Method 3
EXAMPLE 34
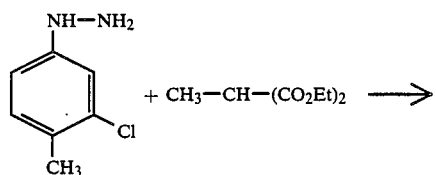
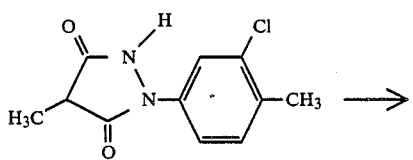
MP = 115° C.
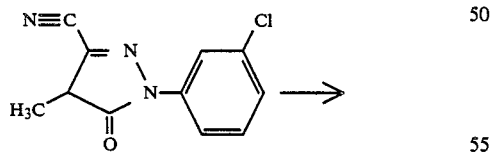
MP = 59° C.
Operating Method 3
EXAMPLE 35
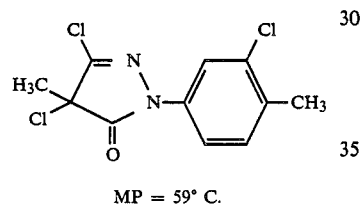
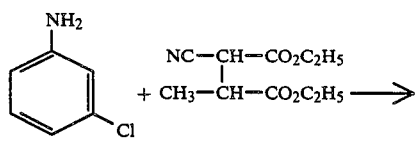
MP = 186–187° C.
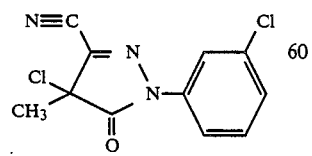
MP = 54~55° C.
Operating Method 4
EXAMPLE 36
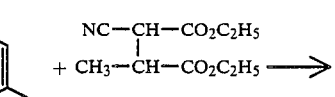
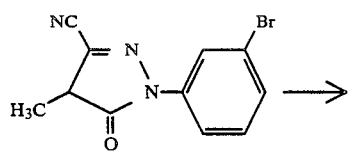
MP = 190° C.
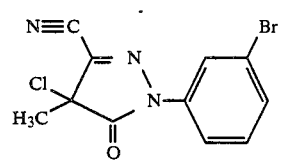
MP = 63~64° C.
Operating Method 4
EXAMPLE 37
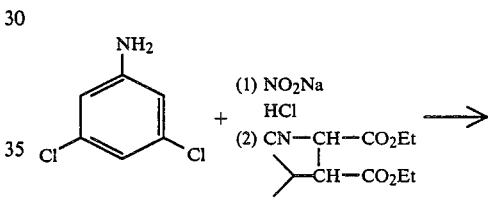
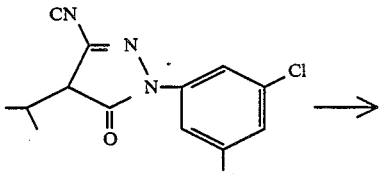
MP = 114° C.
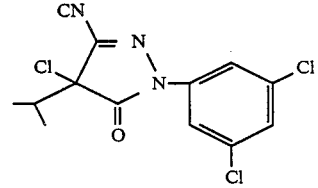
MP = 76° C.
Operating Method 4
EXAMPLE 38
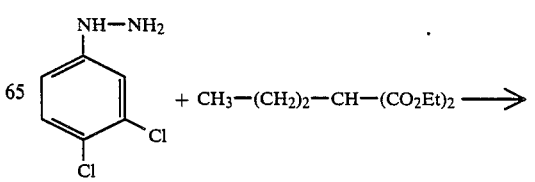

EXAMPLE 39

3-chlorophenylhydrazine + CH₃—(CH₂)₂—CH—(CO₂Et)₂ →

[pyrazolidine-3,5-dione with n-propyl and 3-chlorophenyl]
MP = 102° C.

→ [4,4-dichloro pyrazolinone with n-propyl and 3-chlorophenyl]

Operating Method 3

EXAMPLE 40

4-chloro-3-trifluoromethylphenylhydrazine + CH₃—CH₂—CH—(CO₂Et)₂ →

[pyrazolidine-3,5-dione with ethyl and 4-chloro-3-CF₃-phenyl]
MP = 120° C.

→ [chloro pyrazolinone with ethyl, chloro, and 4-chloro-3-CF₃-phenyl]
MP = 50° C.

Operating Method 3

EXAMPLE 41

4-chloro-3-trifluoromethylphenylhydrazine + CH₃—CH₂—CH₂—CH—(CO₂Et)₂ →

[pyrazolidine-3,5-dione with C₃H₇ and 3,5-dichlorophenyl]
MP = 142° C.

→ [dichloro pyrazolinone with C₃H₇ and 3,5-dichlorophenyl]
MP = 59~60° C.

Operating Method 3

EXAMPLE 42

4-chloro-3-trifluoromethylphenylhydrazine + CH₃—(CH₂)₂—CH—(CO₂Et)₂ →

[pyrazolidine-3,5-dione with n-propyl and 4-chloro-3-CF₃-phenyl]
MP = 116° C.

→ [dichloro pyrazolinone with n-propyl and 4-chloro-3-CF₃-phenyl]

Operating Method 3

EXAMPLE 43

1-(3,4-dichlorophenyl)-3,4-dichloro-4-(1-methyl-propyl)-5-pyrazolone

STEP A:
1-(3,4-dichlorophenyl)-4-(sec-butyl)-pyrazolidine-3,5-dione 50 g of 3,4-dichlorophenylhydrazine (85%) and 122.5 g of diethyl sec-butyl-malonate were heated for 10 hours at 180° C. (external temperature) while distilling 21.3 g of ethanol. The remainder was taken up in 200 ml of methylene chloride, and the solution was extracted with 2N sodium hydroxide, then with water. The combined aqueous phases were washed with methylene chloride and acidified to pH 1 by concentrated hydrochloric acid. The precipitate was separated, washed with water, separated, dried under reduced pressure at 40° C. to obtain 64.8 g of 1-(3,4-dichlorophenyl)-4-(sec-butyl)-pyrazolidine-3,5-dione melting at 118°–120° C.

STEP B:
1-(3,4-dichlorophenyl)-3,4-dichloro-4-(1-methyl-propyl)-5-pyrazolone 30 g of the product of Step A, 120 ml of phosphorus oxychloride and 72 g of phosphorus pentachloride were refluxed for 12 hours, then cooled and poured onto 2 kg of ice. Extraction was carried out with methylene chloride and the extracts were washed with water, dried and brought to dryness. The residue was chromatographed under pressure on silica (eluent: hexane-methylene chloride 8-2) to obtain 4.6 g of 1-(3,4-dichlorophenyl)-3,4-dichloro-4-(1-methylpropyl)-5-pyrazolone.

IR Spectrum (CDCl$_3$): >C=O: 1740 cm$^{-1}$. aromatic: 1593, 1652, 1478 cm$^{-1}$.

EXAMPLE 44

1(3-chloro-4-bromophenyl)-3-trifluoromethyl-4-allyl-4-hydroxy-5-pyrazolone 1 g of 1-(3-chloro-4-bromophenyl)-3-trifluoromethyl-4-allyl-5-pyrazolone in 15 ml of methylene chloride was cooled to 0° C. and 0.25 g of sodium carbonate were added. Then, 0.53 g of m-chloroperbenzoic acid were added and the mixture was held at 0° C. for 3 hours and 30 minutes. The reaction mixture was poured into ice to which sodium hydrogenosulfite had been added and the mixture was extracted with ethyl acetate. The organic phase was washed with a saturated solution of sodium bicarbonate, then with a solution of ammonium sulfate, and finally with water saturated with sodium chloride, dried and concentrated to dryness under reduced pressure. The residue was chromatographed over silica and eluted with methylene chloride to obtain 0.42 g of 1-(3-chloro-4-bromophenyl)-3-trifluoromethyl-4-allyl-4-allyl-4-hydroxy-5-pyrazolone. After crystallization from a methylene chloride-ethanol mixture, the product melted at 100.5° C.

IR Spectrum (CDCl$_3$): OH presence: ~3560 cm$^{-1}$. +associated: ~3400 cm$^{-1}$. >C=O complex: max~1748 cm$^{-1}$; shoulder ~1720 cm$^{-1}$. aromatic: 1616, 1589, 1562, 1474 cm$^{-1}$. C=C: 1640 cm$^{-1}$.

EXAMPLE 45

1-(3-chloro-4-bromophenyl)-3-trifluoromethyl-4-fluoro-4-allyl-5-pyrazolone 4 g of 1-(3-chloro-4-bromophenyl)-3-trifluoromethyl-4-allyl-4-hydroxy-5-pyrazolone in 200 ml of methylene chloride were cooled to −10° C. and 2.7 ml of trifluoride diethylaminosulfide were added all at once. The mixture was stirred for one hour at −10° C./−3° C. 120 ml of a saturated solution of sodium bicarbonate were added and stirring was carried out for 10 minutes, followed by decanting, washing with water, drying and bringing to dryness. The residue was chromatographed on silica and eluted with a hexane-methylene chloride mixture (8-2) to obtain 1.1 g of 1-(3-chloro-4-bromophenyl)-3-trifluoromethyl-4-fluoro-4-allyl-5-pyrazolone.

IR Spectrum (CDCl$_3$): C=O: 1761 cm$^{-1}$. aromatic: 1614, 1590, 1568 cm$^{-1}$. —C=C—: 1644 cm$^{-1}$.

EXAMPLE 46

1-(3,5-dichlorophenyl)-3-chloro-4-fluoro-4-methyl-5-pyrazolone STEP A:
1-(3,5-dichlorophenyl)-3-chloro-4-hydroxy-4-methyl-5-pyrazolone 1 g of 1-(3,5-dichlorophenyl)-3-chloro-4-methyl-5-pyrazolone, 30 ml of ethyl acetate and 1 g of potassium carbonate were cooled to 0° C. and 0.9 g of 75% m-chloroperbenzoic acid were added. The mixture was stirred for 1 hour at 0° C. and the reaction mixture was poured into ice to which sodium hydrogenosulfite had been added. The mixture was extracted with ethyl acetate and the organic phases were washed with a saturated aqueous solution of sodium bicarbonate, then with a solution of ammonium sulfate, and finally with a saturated aqueous solution of sodium chloride, dried and concentrated to dryness under reduced pressure. The residue was dissolved in hot isopropyl ether and pentane was added. Cooling was carried out to obtain 0.97 g of 1-(3,5-dichlorophenyl)-3-chloro-4-hydroxy-4-methyl-5-pyrazolone.

IR Spectrum: OH: 3570 cm$^{-1}$. C=O: 1743 cm$^{-1}$. C=C: 1590 cm$^{-1}$. aromatic: 1570 cm$^{-1}$.

1-(3,5-dichlorophenyl)-3-chloro-4-methyl-5-pyrazolone used in Example 46 was prepared according to the scheme below:

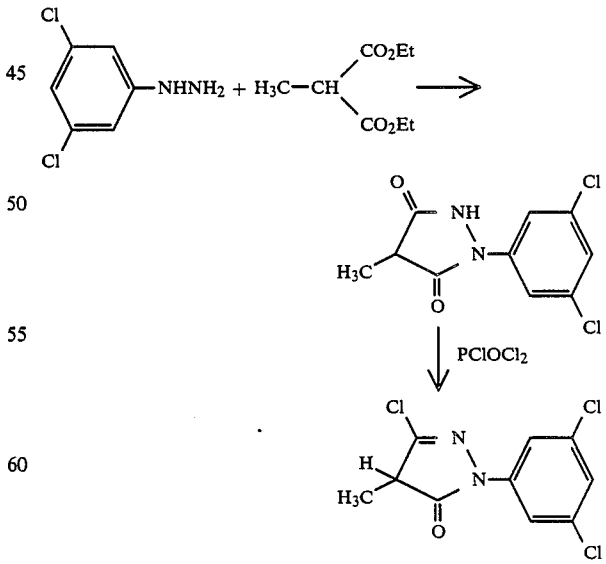

Analysis: C$_{10}$H$_7$Cl$_3$N$_2$O: 277.54

| Calculated: | % C 43.28 | % H 2.55 | % Cl 38.33 | % N 10.1 |

-continued

| Found: | 43.6 | 2.5 | 38.1 | 10.1 |

IR Spectrum: $\nu$C=C: 1600 cm$^{-1}$. aromatic: 1592, 1576, 1526 cm$^{-1}$.

STEP B:
1-(3,5-dichlorophenyl)-3-chloro-4-fluoro-4-methyl-5-pyrazolone 0.85 g of the product of Step A was suspended in 15 ml of methylene chloride and 0.72 ml of trifluoride diethylaminosulfide and after 1 hour of stirring at $-5°$ C., the reaction mixture was poured into an ice-sodium bicarbonate mixture and was extracted with methylene chloride. The extracts were washed successively with saturated solutions of ammonium sulfate and sodium chloride, dried and concentrated to dryness under reduced pressure. The residue was chromatographed over silica (eluent: cyclohexane-isopropyl ether 95-5) to obtain 0.3 g of 1-(3,5-dichlorophenyl)-3-chloro-4-fluoro-4-methyl-5-pyrazolone.

IR Spectrum: C=O: 1753 cm$^{-1}$. C=C: 1588 cm$^{-1}$. aromatic: 1570 cm$^{-1}$.

EXAMPLE 47
1-(3,5-dichlorophenyl)-3-chloro-4-fluoro-4-(1-methylpropyl)-5-pyrazolone

STEP A:
1-(3,5-dichlorophenyl)-3-chloro-4-hydroxy-4-(1-methylpropyl)-5-pyrazolone 0.7 g of 1-(3,5-dichlorophenyl)-3-chloro-4-(1-methylpropyl)-5-pyrazolone and 0.7 g of potassium carbonate were cooled to $-20°$ C. and 0.7 g of 75% m-chloroperbenzoic acid were added all at once. The procedure of Example 46 was followed to obtain 0.34 g of 1-(3,5-dichlorophenyl)-3-chloro-4-hydroxy-4-(1-methylpropyl)-5-pyrazolone used as is for the next step.

1-(3,5-dichlorophenyl)-3-chloro-4-(1-methylpropyl)-5-pyrazolone used in Example 47 was prepared by the scheme below:

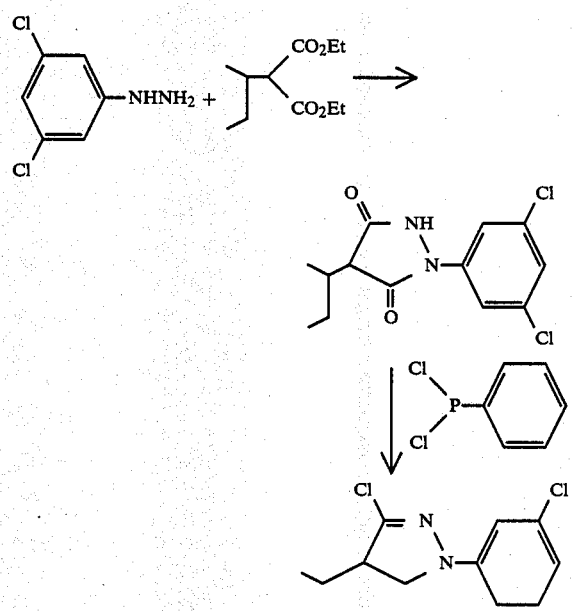

IR Spectrum: $\nu$C=O: 1729 cm$^{-1}$. $\nu$C=C: 1588 cm$^{-1}$. aromatic: 1567 cm$^{-1}$.

STEP B:
1-(3,5-dichlorophenyl)-3-chloro-4-fluoro-4-(1-methylpropyl)-5-pyrazolone 0.25 g of the product of Step A in 20 ml of methylene chloride was cooled to $-20°$ C. and 0.1 ml of trifluoride diethylaminosulfide were introduced. After 30 minutes of stirring at $-20°$ C., the reaction medium was poured into a mixture of ice and sodium bicarbonate and was extracted with methylene chloride. The organic phases were washed successively with saturated solutions of ammonium sulfate and sodium chloride, dried and concentrated to dryness under reduced pressure. The residue was chromatographed over silica and eluted with a cyclohexane-isopropyl ether mixture (95-5) to obtain 0.2 g of 1-(3,5-dichlorophenyl)-3-chloro-4-fluoro-4-(1-methylpropyl)-5-pyrazolone.

NMR Spectrum: 7.65 ppm: H aromatics at 2 and 5.
7.45 ppm: H aromatic at 4.
3.5-3 ppm: H$_1$ of propyl.

EXAMPLE 48
Emulsifiable concentrate

A composition was prepared containing 15% by weight of the product of Example 1, 6.4% by weight of Atlox 4851 (oxyethylene triglyceride combined with a sulfonate, acid value 1.5). 3.2% by weight of Atlox 4855 (oxyethylene triglyceride combined with a sulfonate, acid value 3) and 75.4% of weight of xylene.

EXAMPLE 49
Wettable powder

A wettable powder was prepared containing 25% of the compound of Example 3, 15% of Ekapersol (condensation product of sodium naphthalene sulfonate), 0.5% of Brecolane NVA (alkyl sodium naphthalene sulfonate), 34.5% of Zeozil 39 (synthetic hydrated silica obtained by precipitation) and 25% of Vercoryl "S" (colloidal kaolin).

Study of the pre-emergence herbicide activity

The vegetation used was cultivated in a culture tray (23×14×4 cm) with a double bottom so that watering was effected from underneath. The species are placed at 20 seeds per species in rows 3 cm apart in a single tray using 4 tests for each concentration. The conditions for cultivation were as follows: temperature: 20° C.±2° C., humidity: about 60%, lighting: by fluorescent tube (daylight+brilliant white) from 6 AM to 10 PM each day. The soil mixture was 10 volumes of free soil, 10 volumes of river sand and 2 volumes of peat. The treatment was carried out on the plants above soil after 21 days of cultivation. The product under test was applied under standard conditions with a micro-pulverizer at a quantity of 2.5 kg/ha and a corresponding dilution at 560 l/ha.

A test was carried out with an untreated control and this test contained the same number of seedlings as the treated seedlings. At a quantity of 2.5 to 5 kg of active material per hectare, dicotyledons such as goosefoot. Amaranthus, yellow bedstraw and mustard and monocotyledons such as meadow foxtail were selectively destroyed in cereal crops.

Various modifications of the compounds and method of the invention may be made without departing from the spirit or scope thereof and it is to be understood that the invention is intended to be limited only as defined in the appended claims.

What we claim is:

1. A method of combatting weeds comprising contacting the weeds with a herbicidally effective amount of a compound selected from the group consisting of 1-(3,4-dichlorophenyl)-3,4-dichloro-4-(2-methylpropyl)-5-pyrazolone, 1-(3-chloro-4-bromophenyl)-3-trifluoromethyl-4-chloro-4-methyl-5-pyrazolone, 1,(3,5-dichlorophenyl)-3,4-dichloro-4-methyl-5-pyrazolone and 1-(3,4-dichlorophenyl)-3,4-dichloro-4-n-propyl-5-pyrazolone.

2. A method of selectively killing weeds in cereal crops comprising administering to cereal crops an herbicidally effective amount of at least one compound of 1-(3,4-dichlorophenyl)-3,4-dichloro-4-(2-methylpropyl)-5-pyrazolone, 1-(3-chloro-4-bromophenyl)-3-trifluoromethyl-4-chloro-4-methyl-5-pyrazolone 1,(3,5-dichlorophenyl)-3,4-dichloro-4-methyl-5-pyrazolone and 1-(3,4-dichlorophenyl)-3,4-dichloro-4-n-propyl-5-pyrazolone.

* * * * *